(12) United States Patent  (10) Patent No.: US 7,812,347 B2
Banke, Jr. et al.  (45) Date of Patent: Oct. 12, 2010

(54) INTEGRATED CIRCUIT AND METHODS OF MEASUREMENT AND PREPARATION OF MEASUREMENT STRUCTURE

(75) Inventors: George W. Banke, Jr., Essex Junction, VT (US); Andrew Deering, Swanton, VT (US); Philip V. Kaszuba, Essex Junction, VT (US); Leon Moszkowicz, Milton, VT (US); James Robert, Burlington, VT (US); James A. Slinkman, Montpelier, VT (US)

(73) Assignee: International Business Machines Corporation, Armonk, NY (US)

( * ) Notice: Subject to any disclaimer, the term of this patent is extended or adjusted under 35 U.S.C. 154(b) by 180 days.

(21) Appl. No.: 12/044,030

(22) Filed: Mar. 7, 2008

(65) Prior Publication Data
US 2008/0157077 A1   Jul. 3, 2008

Related U.S. Application Data

(62) Division of application No. 11/160,086, filed on Jun. 8, 2005, now Pat. No. 7,507,591.

(30) Foreign Application Priority Data
Dec. 10, 2002  (WO) ............... PCT/US02/39521

(51) Int. Cl.
   *H01L 23/58* (2006.01)
(52) U.S. Cl. ............................................ 257/48
(58) Field of Classification Search ............ 257/48
   See application file for complete search history.

(56) References Cited

U.S. PATENT DOCUMENTS 5,382,795 A  1/1995  Bayer et al.
5,520,769 A  5/1996  Barrett et al.
5,821,549 A  10/1998  Talbot et al.

(Continued)

FOREIGN PATENT DOCUMENTS

JP   7211757   8/1995

(Continued)

OTHER PUBLICATIONS

Takigami et al., "Measurements of the three dimesnional impurity profile in Si using chemical etching and scanning tunneling microscopy", May 1991, Appl. Phys. Lett., vol. 58, No. 20, pp. 2288-2290.*

(Continued)

*Primary Examiner*—Evan Pert
(74) *Attorney, Agent, or Firm*—Ian MacKinnon; Roberts Mlotkowski Safran & Cole, P.C.

(57) ABSTRACT

A method for measuring an integrated circuit (IC) structure by measuring an imprint of the structure, a method for preparing a test site for the above measuring, and IC so formed. The method for preparing the test site includes incrementally removing the structure from the substrate so as to reveal an imprint of the removed bottom surface of the structure in a top surface of the substrate. The imprint can then be imaged using an atomic force microscope (AFM). The image can be used to measure the bottom surface of the structure.

19 Claims, 6 Drawing Sheets

U.S. PATENT DOCUMENTS

| | | | |
|---|---|---|---|
| 6,054,710 A | 4/2000 | Bruggeman | |
| 6,200,866 B1 * | 3/2001 | Ma et al. | 438/299 |
| 6,250,143 B1 | 6/2001 | Bindell et al. | |
| 6,489,611 B1 | 12/2002 | Aumond et al. | |

FOREIGN PATENT DOCUMENTS

| | | |
|---|---|---|
| WO | WO02/075806 | 9/2002 |

OTHER PUBLICATIONS

Morimoto et al, "New Atomic Force Microscope for Critical Dimension Metrology with Carbon Nanotube", Microprocesses and Nanotechnology 2002, Nov. 8, 2002, pp. 10-11.

Ridley et al, "The Implementation of AFM for Process Monitoring and Metrology in Trench MOSFET Device Manufacturing", 2002 IEEE/SEMI Advanced Semiconductor Manufacturing Conference, pp. 408-414.

Raineri et al., "Carrier Distribution in Silicon Devices by Atomic Force Microscopy on Etched Surfaces", Appl. Phys. Lett. 64 (3) Jan. 17, 1994, pp. 354-356.

* cited by examiner

INTEGRATED CIRCUIT AND METHODS OF MEASUREMENT AND PREPARATION OF MEASUREMENT STRUCTURE

CROSS REFERENCE TO RELATED APPLICATIONS

This patent application is a divisional patent application of pending, U.S. patent application Ser. No. 11/160,086, entitled "Integrated Circuit and Methods of Measurement and Preparation of Measurement Structure" filed Jun. 8, 2005, which claims the benefit of PCT Patent Application No. PCT/US02/39521, entitled "Integrated Circuit and Methods of Measurement And Preparation of Measurement Structure," filed on Dec. 10, 2002.

TECHNICAL FIELD

The technical field of the invention is physical measurement of an integrated circuit.

DESCRIPTION OF THE PRIOR ART

Very large-scale integration (VLSI) technology requires knowledge of chip critical dimension (CD) and failure analysis (FA) data in order to monitor and debug devices. For example, the critical dimensions of complementary metal-oxide semiconductor (CMOS) polysilicon gate conductor (PC) and the associated polysilicon spacer dimensions are normally important relative to those devices.

Unfortunately, current measurement technology suffers from a number of drawbacks. For instance, non-destructive measurement techniques, such as an in-line scanning electron microscope (SEM), are not representative of the critical dimension of interest since the data is taken before processing is complete. Similarly, destructive techniques such as transmission electron microscopy (TEM) require perpendicular cross-sectioning of a sample for measurement, which is labor intensive and time consuming. In addition, destructive techniques generally only measure in one-dimension which may not be representative of the CD of the entire structure. Electrical measurement has been found to be an accurate measurement technique if the data is properly de-convoluted. However, it is expected that at gate lengths of less than 50 nm, the electrical measurement technique will not be accurate due to parasitic capacitances.

The above-mentioned techniques do not allow for dimension data over the entire span of a PC structure that would allow for detection of: systematic variations in dimensions; local anomalies such as misalignment; PC narrowing or widening; or defects such as bumps and depressions. In addition, SEM data is limited in cross-section and somewhat inaccurate in plan-view.

Another disadvantage of current measurement technology, except after PC etch, is that it currently does not allow for in-line implementation, nor measurement at the end-of-process. Obtaining an accurate CD measurement at the end-of-process is more desirable because this measurement relates directly to electrical performance.

In view of the foregoing, there is a need in the art for an improved method of measuring a semiconductor CD.

SUMMARY OF THE INVENTION

The invention relates to a method for measuring an integrated circuit structure by measuring an imprint of the structure, a method for preparing a test site for the above measuring, and the integrated circuit so formed. The method for preparing the test site includes removing a portion of the structure from the substrate so as to reveal an imprint of the removed bottom of the structure in a top surface of the substrate. The imprint can then be imaged using an atomic force microscope (AFM), which can be used to measure the bottom of the structure and to determine the CD. The test site preparation can be implemented for in-line measurement of structures at arbitrary locations on arbitrary dies on a wafer so as to account for chip-to-chip variations of the structure across the entire span of the wafer. The invention allows for observation in plan-view in two dimensions to an accuracy of at least 4 nm, and is extendable to overall dimensions of less than 50 nm. The invention also may reduce the total analysis time (e.g., sample preparation, data collection, data reduction) by roughly 25% that of existing techniques.

The foregoing and other features of the invention will be apparent from the following more particular description of embodiments of the invention.

BRIEF DESCRIPTION OF THE DRAWINGS

The embodiments of this invention will be described in detail, with reference to the following figures, wherein like designations denote like elements, and wherein.

DESCRIPTION OF THE PREFERRED EMBODIMENT

Figure 1:
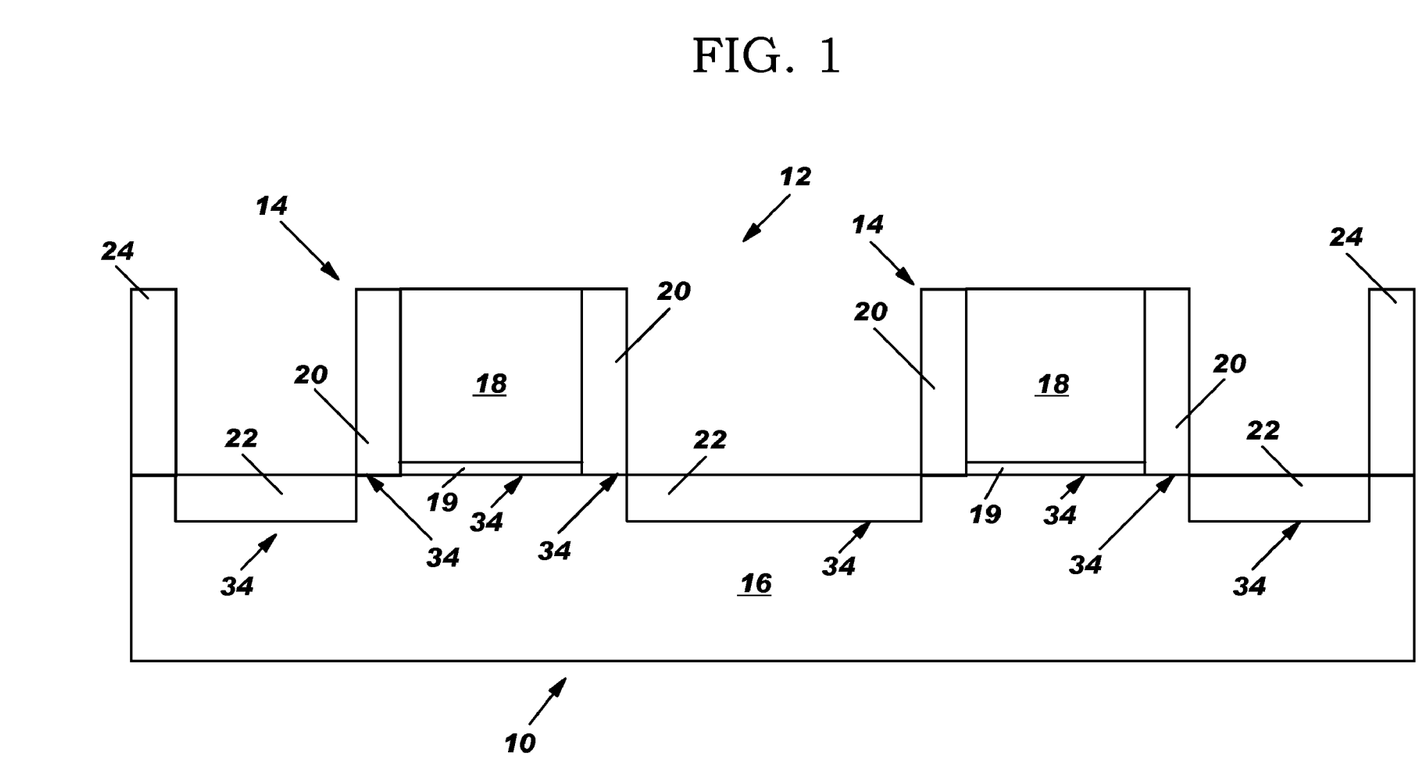
FIG. 1 shows an IC including a structure to be measured.

With reference to the accompanying drawings, FIG. 1 shows an integrated circuit (IC) 10 including one embodiment of a structure 12 to be measured. In the exemplary embodiment shown, structure 12 includes a pair of field effect transistors (FET) 14 and other IC components 24 positioned upon a substrate 16. Substrate 16 is preferably made of silicon. Each FET 14 includes a gate conductor 18 sitting upon a gate oxide 19 between a pair of spacers 20. A source-drain region 22 extends between each FET 14. Other components 24 of IC 10 are also shown. Although not shown for clarity, all of the components extend into the page to some extent. It should be recognized that the form of the structure to be measured can vary drastically, i.e., it is not necessarily a FET. Other possible structure include, for example, an isolation trench, a contact hole, an active silicon region, a dynamic random access memory (DRAM) storage node trench opening, a silicide footprint, a diffusion resistor dimension, etc. In addition, it should be recognized that structure 12 shown has been simplified for purposes of brevity and clarity.

Figure 2:
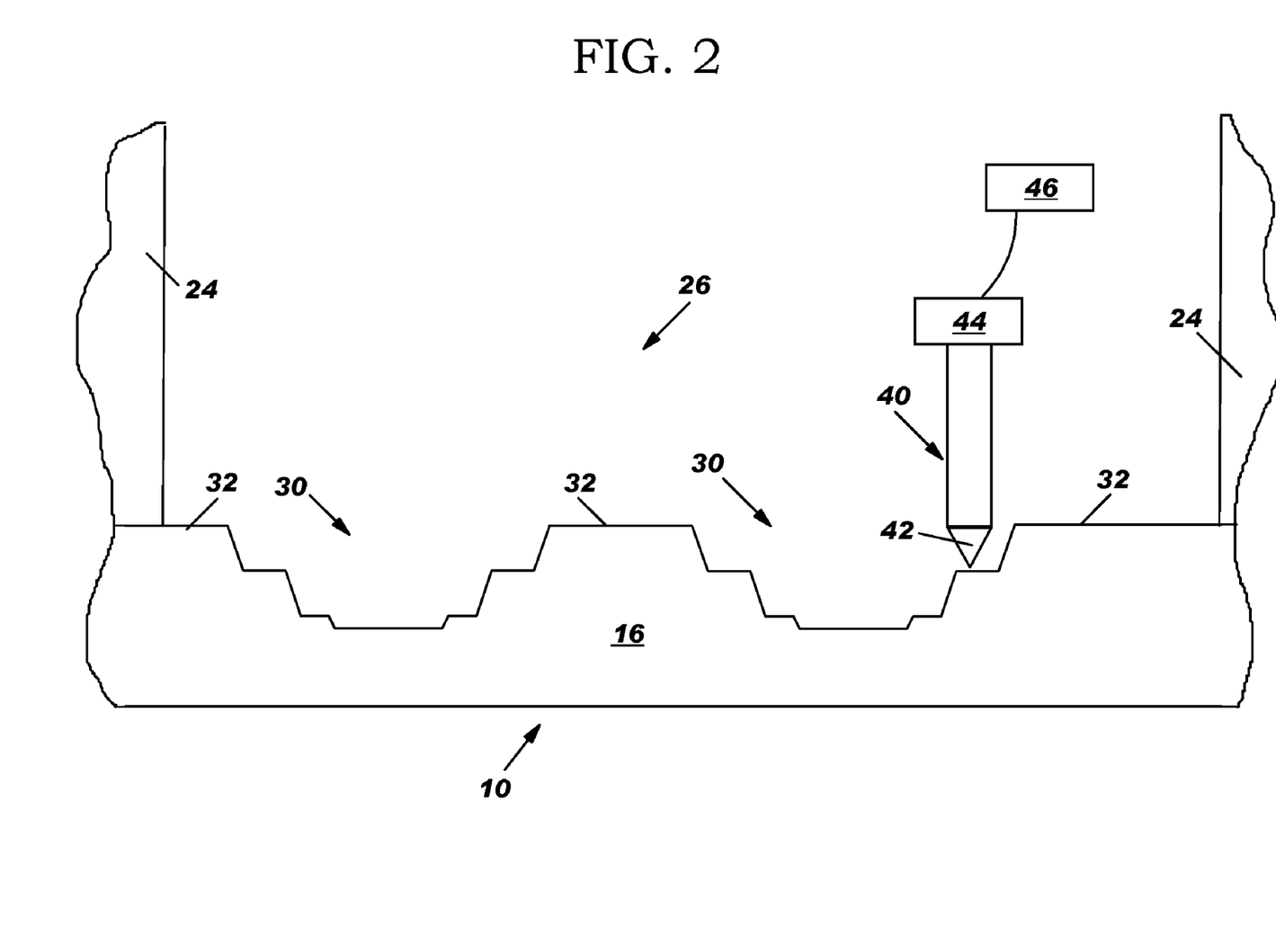
FIG. 2 shows a test site of the IC of FIG. 1 including an imprint.

Referring to FIG. 2, one embodiment of a test site 26 for measuring of structure 12 of IC 10 is shown. Test site 26 includes a microscopic imprint 30 (greatly enlarged in FIG. 2) that is generated by the removal of structure 12 in a top surface 32 of substrate 16. Imprint 30 is horizontally (across and into page) a replica of a bottom surface 34 (FIG. 1) of structure 12, and is formed in top surface 32 (FIG. 2) of substrate 16 when any structure 12 is formed upon a substrate 16. Removal of structure 12 to top surface 32 reveals imprint 30. As shown in FIGS. 1 and 2, structure 12 and accordingly bottom surface 34 may include a number of segments, each of which forms its own share of imprint 30. The horizontal dimensions of imprint 30 are identical to the dimensions of bottom surface 34 of structure 12 to within the precision of the removal process. Accordingly, measurement of the dimensions of imprint 30 provide the measurements of the removed bottom surface of corresponding parts of structure 12.

As noted above, in order to prepare test site 26 for measuring, imprint 30 must be revealed by removal of structure 12. As used herein, "removal of structure" means a horizontally extending part of structure 12 which is removed by the following described processes. The entirety of a structure 12, as it extends horizontally, need not be removed. In one embodiment, removal is provided by incrementally removing portions of structure 12 down to top surface 32. That is, remove a portion of structure 12 and then repeat the step of removing until imprint 30 in top surface 32 is revealed. Incremental removal allows clearance of a portion of structure 12 without damage to substrate 16, i.e., it is intact.

Test site 26 may be isolated from other components 24 of IC 10 in a number of ways. If it is appropriate to remove test site 26 from IC 10, then test site 26 can be cut from a larger sample of IC 10 and, for example, affixed to a silicon slide for preparation. Affixation may be provided, for example, using wax. Preparation of test site 26 may begin with precursor de-layering of upper sections of polysilicon by any well known or later developed processes of removal. Once to this point, in this embodiment, it has been found advantageous to incrementally remove portions of structure 12 by repeatedly agitating test site 26 in a hydrofluoric (HF) acid bath. That is, remove remaining overlying films to leave imprint 30. Agitation can be provided in any now known or later developed fashion. One way of agitating is to use a magnetic agitator operating at approximately 100-1000 RPM. In one embodiment, it has also been found advantageous to maintain HF acid at a temperature in the range of 18° C.-22° C., and preferably at about 21° C. Each agitating step, i.e., removal step, is shortened in duration compared to a preceding agitating step. Actual durations used will vary depending on structure 12 makeup. Exemplary durations may include approximately 30 seconds per layer and start at approximately 3 minutes. After each agitating step, test site 26 is rinsed with water, e.g., de-ionized water, and thereafter dried, e.g., using blown clean dry air or nitrogen. Subsequently, any foreign material on test site can be removed using a replication film or transparent tape. It should be recognized that the above-described technique for incrementally removing structure 12 is not the only method available to complete the process. Accordingly, the invention should not be limited to this particular technique other than as provided in the attached claims. In addition, the above exemplary embodiment may be varied for implementation in a manufacturing setting.

In other situations, it may be inappropriate or disadvantageous to remove test site 26 from IC 10. In this case, test site 26 may be prepared in-situ on IC 10 with the resulting IC including imprint 30 of removed bottom surface 34 of structure 12 in top surface 32 of substrate 16. Test site 26 would be included in a design as an operationally unrequired portion of IC 10 but fabricated using the same established techniques as other operational components. Test site 26 may then be protected using an extra mask from the back-end-of-line (BEOL) processes. Removal of structure 12 for measurement may then be provided using a controlled HF acid similar to that described above but without removal of test site 26. In this way, removal of structure 12 in test site 26 would not harm operation of other components 24 of IC 10. It is in this fashion that structure 12 of IC 10 can be measured in-line without destroying IC 10.

Once imprint 30 has been revealed, bottom surface 34 of structure 12 can be measured by measuring imprint 30. As shown in FIG. 2, in one embodiment, measurement is provided by taking a three dimensional image of imprint 30 by scanning using an atomic force microscope (AFM) 40. In one embodiment, AFM 40 is a 1-dimensional AFM implemented to attain a three dimensional image. An AFM is a well-known type of scanning probe microscope including a sensor section 44 coupled to a probe 42 and a data processor section 46. As known to those skilled in the art, an AFM creates a high resolution three-dimensional image. Measurement using AFM 40 may include precursor steps such as measurement of structure on known linear dimensions, e.g., an NIST traceable standard (e.g., a pitch control grid), to calibrate AFM 40 prior to use. In addition, measurement of the known linear dimensions may be conducted after use to ensure probe 42 has not been damaged or that AFM 40 drive control mechanism (not shown) has not drifted during use. In one embodiment, actual measurement is conducted using an unused probe 42.

Figure 3:
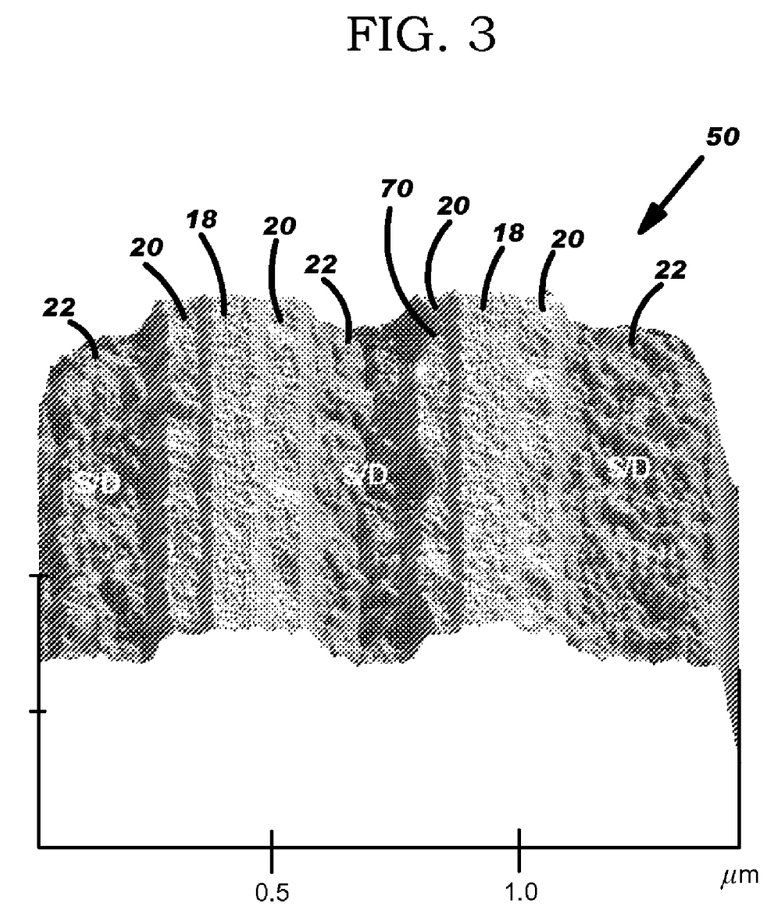
FIG. 3 shows a three-dimensional image of the imprint of FIG. 2.

FIG. 3 shows an exemplary three-dimensional image 50 of test site 26. In the example shown, image 50 has been digitally modified to better show relief by providing a point of light and rotation to a partial perspective view. Image 50 shows the topography of imprint 30 including that of bottom surfaces 34 of FETs 14 (FIG. 1) including gate conductors 18, spacers 20 and source-drain regions 22. Based on this data, dimensions of, for example, gate length and spacer width can be ascertained.

Figure 4A:
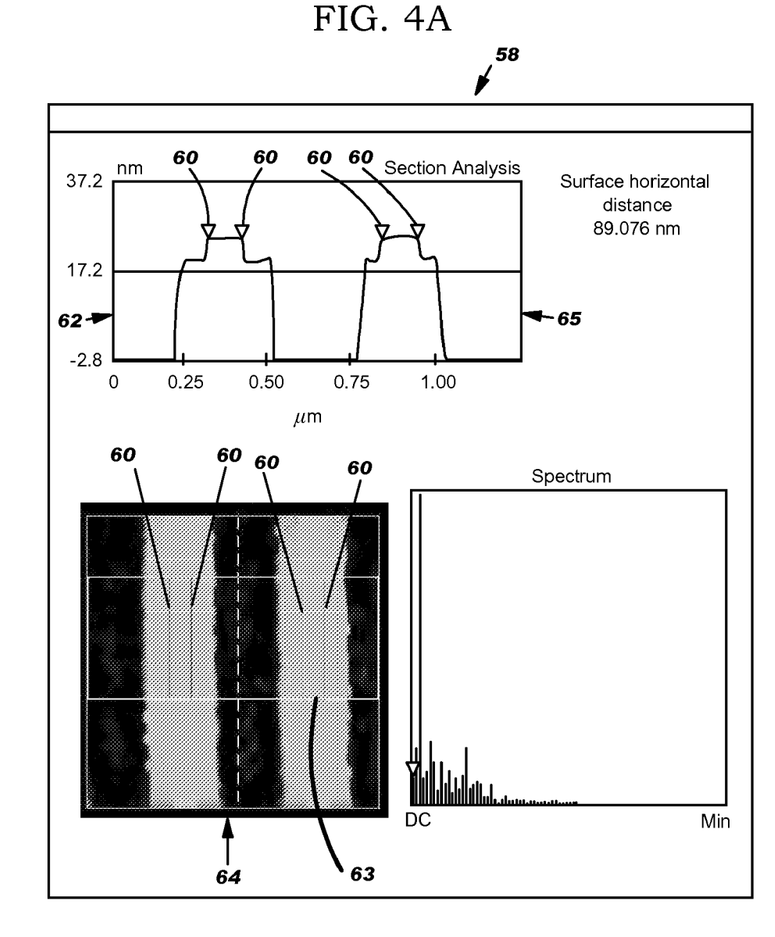
FIGS. 4A-4C show graphical user interfaces of data analysis.
Figure 4B:
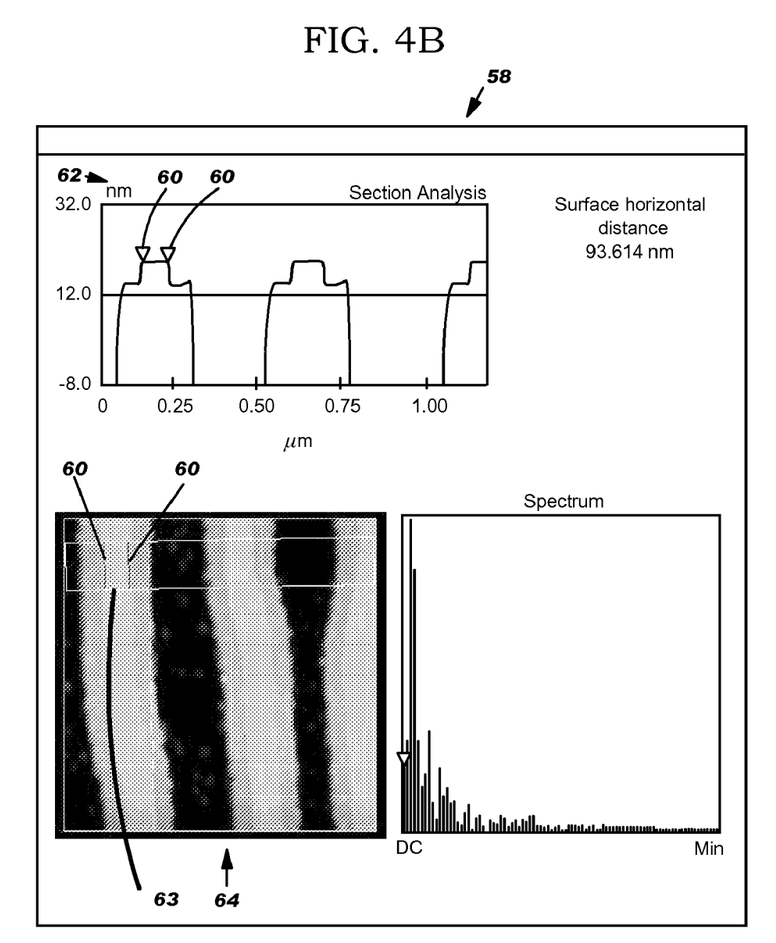
Figure 4C:
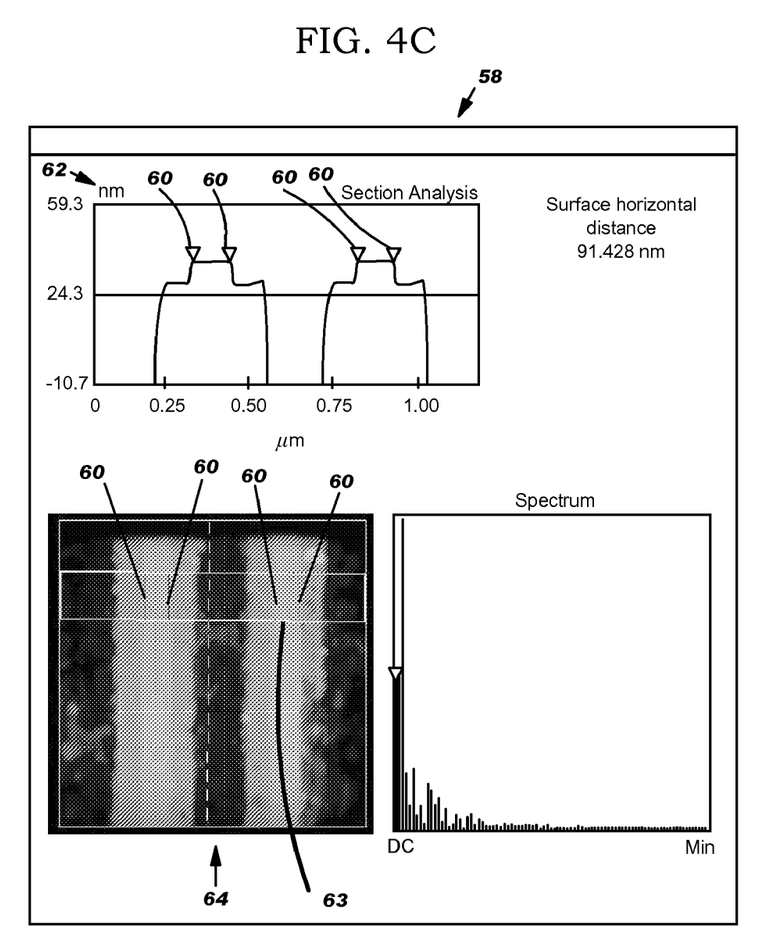

FIGS. 4A-4C show graphical user interfaces (GUIs) 58 provided by AFM 40 processing software and showing data analysis. FIG. 4A shows an in-line test ("ILT") poly CD kerf structure; FIG. 4B shows imprints of poly gate lines in a gate array on the same die; and FIG. 4C shows imprints of poly gate lines on a kerf performance circuit. Conventional AFM 40 processing software allows for data interpretation and dimensional calculations. For example, each of FIGS. 4A-4C includes a section analysis area 62 in which a sectional representation 64 of an image (lower left corner) is provided. Each sectional representation 64 shows a section of image 50 (FIG. 1) under evaluation and allows for selective placement of a test window 63. A cross-section image area 65 (upper left corner) includes pointers 60 (down arrows) that match the left-right extremities of test window 63. AFM 40 software is capable of computing a dimension within test window 63, e.g., between pointers 60, in a number of statistical fashions such as averaging. Accordingly, the measured dimension can be determined over a two-dimensional area, which is a more precise representation of a functional device than a mere one-dimensional cross-sectional snapshot. The results of measurement are shown in the right of each GUI 58. In FIG. 4A, gate 18 (FIG. 1) length is reported as 89.074 nm+/−4 nm; in FIG. 4B, the length is reported as 93.614 nm+/−4 nm; and in FIG. 4C, the length is reported as 91.421 nm+/−4 nm. A variety of other data reporting, as shown, and statistical calculations are all easily provided by conventional software, e.g., Digital Instruments Image Processing Software V5.12R2.

In addition to actual dimensions, image 50 (FIG. 3) also allows detection of defects such as an anomaly and/or a photolithographic misalignment. Defects can be determined through dimensional interpretation and visually. In terms of the latter technique, each of FIGS. 4A-4C also includes a sectional image area 64 showing a part of image 50 (FIG. 3) under review. Referring to FIG. 4B, although the curved lines in image area 64 are purposefully provided, it is clear that defects can be easily detected visually in image area 64. In addition, in some cases, defects can be detected in image 50 (FIG. 3). For example, rounded areas 70 in image 50 indicate misaligned contacts.

The above-described method for measuring an IC structure, method for preparing a test site, and IC so formed, allow for accurate measurement/detection of, for example, polysilicon line edge roughness (LER), and field effect transistor (FET) channel dimensions (length and width), sidewall spacer dimensions (length and width), and overlay measurements at the silicon level on a single selected device located anywhere on a chip. In addition, FET channel anomalies such as local widening or narrowing, and FET channel defects such as bumps or depressions, can now be accurately quantified. The invention can be implemented for in-line measurement of structures at arbitrary locations on arbitrary dies on a wafer. The invention allows for observation in plan-view in two dimensions to an accuracy of at least 4 nm, and is extendable to overall dimensions of less than 50 nm. The invention also may reduce the total analysis time (e.g., sample preparation, data collection, data reduction) by roughly 25% that of existing techniques.

While this invention has been described in conjunction with the specific embodiments outlined above, it is evident that many alternatives, modifications and variations will be apparent to those skilled in the art. Accordingly, the embodiments of the invention as set forth above are intended to be illustrative, not limiting. Various changes may be made without departing from the spirit and scope of the invention as defined in the following claims.

The invention claimed is:

1. An integrated circuit (IC) including a test site for measurement of a bottom surface of a structure of the IC, the IC comprising:
    an imprint of a removed bottom surface of the structure in a top surface of the substrate, wherein the imprint includes a plurality of segments having differing respective depths,
    whereby an image of the imprint can be used to measure the structure.

2. The IC of claim 1, wherein the imprint is revealed by incrementally removing the structure to the top surface.

3. The IC of claim 2, wherein each incremental removal is provided by agitating the test site in hydrofluoric acid.

4. The IC of claim 1, wherein the plurality of segments correspond to a plurality of different components of the structure.

5. The IC of claim 1, wherein the plurality of segments correspond to a gate conductor, sidewall spacers, and source drain regions of the structure.

6. The IC of claim 1, wherein the structure is one of:
    an isolation trench;
    a contact hole;
    an active silicon region;
    a dynamic random access memory storage node trench opening;
    a silicide footprint; and
    a diffusion resistor.

7. The IC of claim 1, wherein the test site is cut from a sample of an integrated circuit.

8. The IC of claim 7, wherein the test site is affixed to a silicon slide.

9. The IC of claim 8, wherein wax affixes the test site to the silicon slide.

10. The IC of claim 1, wherein the test site is included in an operationally-unrequired portion of an integrated circuit.

11. The IC of claim 10, wherein the test site is structured and arranged to provide in-line measurement without destroying the integrated circuit.

12. An integrated circuit, comprising:
    a substrate having a top surface; and
    an imprint in the top surface of the substrate where a structure has been removed from the substrate,
    wherein a topography of the implant includes:
        a first segment corresponding to a removed gate conductor of the structure;
        a second segment corresponding to a removed sidewall spacer of the structure; and
        a third segment corresponding to a removed source drain region of the structure.

13. The integrated circuit of claim 12, wherein:
    a width of the first segment corresponds to a gate length dimension; and
    a width of the second segment corresponds to a sidewall spacer width dimension.

14. The integrated circuit of claim 13, wherein:
    the first segment is at a first depth;
    the second segment is at a second depth that is different from the first depth; and
    the third segment is at a third depth that is different from the first depth and the second depth.

15. The integrated circuit of claim 14, wherein a test site comprising the imprint is located on a structure that is cut from a sample of an integrated circuit.

16. The integrated circuit of claim 15, wherein the test site is affixed to a silicon slide.

17. The integrated circuit of claim 16, wherein wax affixes the test site to the silicon slide.

18. The integrated circuit of claim 14, wherein a test site comprising the imprint is included in an operationally-unrequired portion of an integrated circuit.

19. The integrated circuit of claim 18, wherein the test site is structured and arranged to provide in-line measurement without destroying the integrated circuit.

* * * * *